United States Patent [19]

Bur et al.

[11] Patent Number: 5,151,748
[45] Date of Patent: Sep. 29, 1992

[54] OPTICAL SENSOR FOR THE MEASUREMENT OF MOLECULAR ORIENTATION AND VISCOSITY OF POLYMERIC MATERIALS BASED ON FLUORESCENCE RADIATION

[75] Inventors: Anthony J. Bur, Rockville, Md.; Robert E. Lowry, Falls Church, Va.; Steven C. Roth, Frederick, Md.; Charles L. Thomas, Philadelphia, Pa.; Francis W. Wang, Gaithersburg, Md.

[73] Assignee: The United States of America as represented by the Secretary of Commerce, Washington, D.C.

[21] Appl. No.: 563,762

[22] Filed: Aug. 7, 1990

[51] Int. Cl.$^5$ .............................. G01N 21/64
[52] U.S. Cl. .................... 356/32; 73/54.01; 73/53.01; 356/364
[58] Field of Search ........... 356/32, 318, 364, 367, 356/368, 369; 250/453.1, 459.1; 73/54

[56] References Cited

U.S. PATENT DOCUMENTS

| | | |
|---|---|---|
| 3,565,870 | 2/1971 | Iino . |
| 4,113,384 | 9/1978 | Lauer et al. ............... 356/70 |
| 4,521,111 | 6/1985 | Paulson et al. ............ 356/367 |
| 4,605,587 | 8/1986 | Ninomiya et al. .......... 250/560 |
| 4,651,011 | 3/1987 | Ors et al. ................. 356/368 |
| 4,802,762 | 2/1989 | Hill, Jr. .................. 356/318 |
| 5,037,763 | 8/1991 | Petisce .................. 250/459.1 |

OTHER PUBLICATIONS

Nobbs et al, Polymer 15, 287 (1974).
Jarry et al, J. Poly. Sci., Ply. Phys., 1879 (1980).
Chappoy et al, Macromolecules, 12, 680 (1978).
Chappoy et al, Method of experimental Physics, vol. 16a, Academic Press, New York (1980).

Primary Examiner—Richard A. Rosenberger
Attorney, Agent, or Firm—Steven A. Becker; Michael S. Gzybowski

[57] ABSTRACT

A method of measuring fluid properties of a polymer melt, undergoing shear and/or extensional flow which utilizes fluorescent anisotropy. The method utilizes a polymeric chromophore which includes a bifunctional anthracene that is covalently bonded to polybutadiene. The invention also involves an optical probe which is designed to be inserted into existing temperature and/or pressure probe ports in processing equipment. The probe includes a rotatable polarizer and emission collection fibers.

7 Claims, 4 Drawing Sheets

OPTICAL SENSOR FOR THE MEASUREMENT OF MOLECULAR ORIENTATION AND VISCOSITY OF POLYMERIC MATERIALS BASED ON FLUORESCENCE RADIATION

TECHNICAL FIELD

The present invention relates to an apparatus and methods for measuring properties of a polymer melt. In particular, the present invention relates to an apparatus and methods for measuring molecular orientation and non-Newtonian viscosity, of a polymer melt undergoing shear and/or extensional flow.

BACKGROUND ART

A fundamental property of polymer melts is their non-Newtonian viscosity, i.e., as applied shear rate increases, the shear viscosity decreases. The underlying molecular cause of this effect is molecular orientation in the direction of flow. A measurement of molecular orientation at a given value of shear rate can be used to deduce the value of the non-Newtonian viscosity. Optical parameters which can be used to monitor molecular orientation are birefringence, dichroism, and fluorescence anisotropy. The first two measurements require the transmission of light through the subject polymer material, but fluorescence anisotropy can be measured via excitation and detection from the same surface. Because of this, fluorescence measurements can be carried out on opaque or translucent filled polymers by examining the "front" surface. A single probe, used to excite and collect fluorescence light, is sufficient for the fluorescence observations.

If a polymer contains fluorescent moieties within its structure, then fluorescence anisotropy measurements can be made without adding a tracer dye. However, most polymer materials are not inherently fluorescent and the incorporation of a dye is necessary in order to use fluorescence to monitor the properties of interest. For application of fluorescence monitoring, the dye must have a molecular weight or aspect ratio high enough so that it can reflect the polymer-like behavior of the polymer matrix such as molecular orientation under the influence of an applied shear and/or extensional stresses.

The use of fluorescence measurements to monitor the molecular orientation is the subject of U.S. Pat. No. 4,521,111 to C. M. Paulson and M. E. Faulhaber. Their technique consists of monitoring the fluorescence intensity as the excitation polarizer is continuously rotated. When the direction of excitation light is coincident with the average direction of the fluorescence absorption vector, maximum fluorescence intensity is observed. When examining an oriented specimen, a sinusoidally alternating intensity is generated by this technique. However, this method does not yield values of the fluorescence anisotropy and moments of the distribution. Also, Paulson and Faulhaber do not attempt to measure non-Newtonian viscosity.

Fluorescence has been used to measure the molecular orientation in solid polymer films (Nobbs et al., *Polymer*, 15, 287 (1974) and Jarry et al., *J. Poly. Sci., Poly. Phys*, 18, 1879 (1980)) and in the processing of polymer fibers (Chappoy et al., *Macromolecules*, 12, 680 (1979)), but fluorescence techniques have not been employed to measure non-Newtonian viscosity of polymer melts and/or solutions undergoing shear flow.

On-line, real-time monitoring of the viscosity during the processing of polymer products is a necessary requirement for many manufacturers. Optimizing the viscosity in relation to other processing parameters can yield increased productivity and improved product performance. Knowledge of the molecular orientation can be used to predict and control the anisotropic character of the mechanical and electrical properties of the final product.

Current methods for measuring viscosity involve intrusive probes which disrupt the material flow or involve off-line units to which material is pumped from the main line. One advantage of the technique according to the present invention is that nonintrusive fluorescent measurements of viscosity can be carried out on-line.

DISCLOSURE OF THE INVENTION

It is accordingly the object of the present invention to provide an apparatus for measuring properties of a polymer melt which utilizes fluorescence anisotropy.

It is another object of the present invention to provide an apparatus which utilizes fluorescence anisotropy to measure molecular orientation and non-Newtonian viscosity of a polymer melt undergoing shear and/or extensional flow.

It is a further object of the present invention to provide for a polymeric chromophore which can be utilized to measure fluorescence anisotropy and non-Newtonian viscosity of a polymer melt.

It is a still further object of the present invention to provide for a polymeric chromophore which may be incorporated into a polymer matrix whereby the polymeric chromophore orients with the matrix polymer orientation.

It is a still further object of the present invention to provide a method for measuring properties of a polymer melt which utilizes fluorescence anisotropy.

It is a still further object of the present invention to provide a method for measuring non-Newtonian viscosity, molecular orientation, shear rate, extensional rate, extensional stress, and shear stress of a polymer melt which utilizes fluorescence anisotropy.

According to the present invention, there is provided a polymeric chromophore which can be incorporated into a polymer melt and which further exhibits sensitivity to processing parameters which result from molecular orientation of the polymer melt.

The polymeric chromophores of the present invention are incorporated into polymer matrix melts and utilized in fluorescence anisotropy measurement procedures to determine molecular orientation, non-Newtonian viscosity and various processing parameters occurring in the polymer melt.

The present invention also relates to a flow apparatus and an optical probe which can be utilized to measure fluorescence anisotropy of a flowing material and detect changes that occur on the molecular scale.

BRIEF DESCRIPTION OF DRAWINGS

The present invention will now be described with reference to the annexed drawings, which are given by way of non-limiting examples only in which.

BEST MODE FOR CARRYING OUT THE INVENTION

Figure 1:
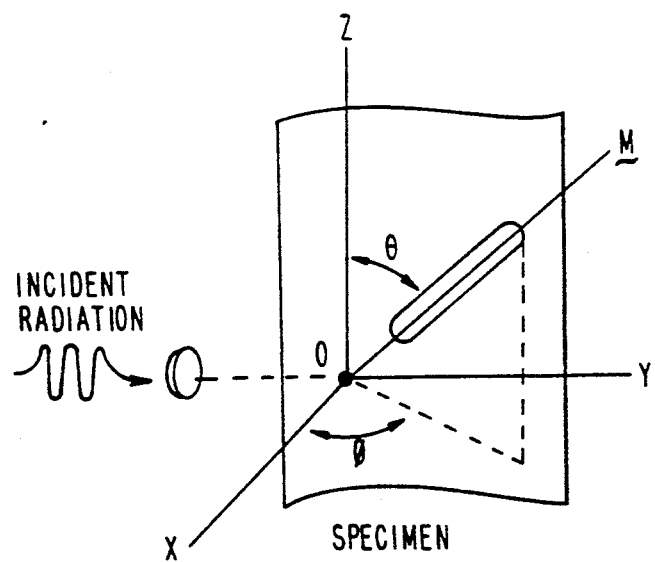
FIG. 1 is an illustration of the laboratory coordinate system with the molecular axis of the chromophore according to the present invention.

The technique of the present invention involves the excitation of fluorescent chromophores which are oriented in a polymer matrix and the subsequent monitoring and analysis of the resulting fluorescence spectra. Since polymer binders are not naturally fluorescent, it is necessary to dope the processing ingredients with a low concentration of fluorescent chromophores which are added as separate entities or chemically bound to the binder. In this regard, a chromophore is chosen in accordance with its sensitivity to the processing parameters of interest. To monitor several processing parameters, a separate chromophore for each parameter may be employed. It is necessary that the fluorescence spectra be obtained with extremely low concentrations of chromophore in the binder ($10^{-4}$ to $10^{-6}$ molar), otherwise their presence might affect the material properties of the final product.

The ultimate application of fluorescence spectroscopy according to the present invention involves an on-line, non-destructive probe for real-time monitoring of processing parameters. As discussed in detail below, this probe involves optical fibers which are employed to transmit and receive optical energy to and from various monitoring sites in processing equipment. Optical energy which is sent to the monitoring site excites nearby chromophores which respond by radiating characteristic spectra. From an analysis of the spectra, processing conditions at the probe site are determined.

In order to observe polymer materials properties, such as non-Newtonian viscosity, from fluorescence spectroscopy observations, it is necessary to use a chromophore which is covalently bonded to the polymer backbone. Many fluorescent dyes are available commercially, but these known dyes all are low molecular weight species and do not fit the criteria for the present invention. The polymeric chromophore which has been designed for the fluorescence spectroscopy measurements of the present invention is derived from a bifunctional anthracene which is covalently bonded to polybutadiene so that the fluorescently active anthracene resides at a central position on the polymer main chain.

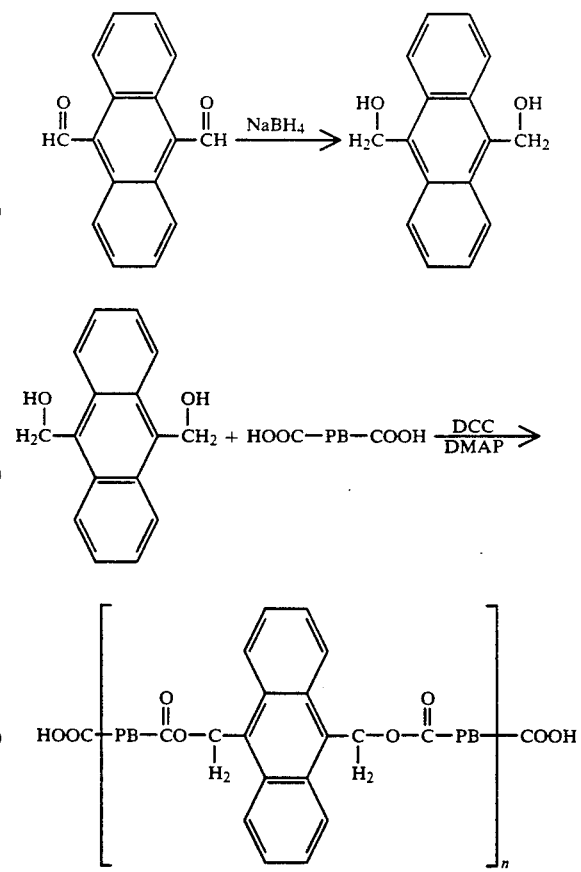

PB - Polybutadiene ($M_w$ = 12,000)
NaBH$_4$ - sodium borohydride
DCC - dicyclohexylcarbodiimide
DMAP - dimethylaminopyridine In this chemical synthesis 9,10 dicarboxyl terminated anthracene is first converted to anthracene dimethanol. The anthracene is next covalently bonded to a dicarboxyl terminated polybutadiene via an esterification reaction. The number average molecular weight of the starting polybutadiene was 6000. The synthesized product has been characterized using gel permeation chromatography (GPC) and infrared analysis. Infrared spectra has showed that: (a) the reaction to convert the dicarboxyl anthracene to anthracene dimethanol yielded the desired product; and, (b) the esterification reaction to covalently bond anthracene to the polybutadiene proceeded as planned. The conversion of the dicarboxyl terminated anthracene to dimethanol anthracene was seen in the elimination of the carboxyl absorption at 1280 cm$^{-1}$ and the creation of the C—O stretch of the alcohol. Confirmation of the esterification reaction was obtained from the observation of the creation of the ester carboxyl line at 1734 cm$^{-1}$.

An analyzed GPC trace of the polymeric chromophore (GPC detector output versus the elution volume) showed that the product, polybutadiene+anthracene, had a molecular weight which was approximately twice that of the starting material and its molecular weight distribution was somewhat broader. Analysis of the data showed that the number average molecular weight of the product was approximately 12,000 and its weight average was approximately 30,000. It was thus concluded that $n \approx 1$, i.e., there is one anthracene per polymer chain and it is positioned in the center of the main chain. The polymeric chromophore was called a labelled polybutadiene and it was used in the molecular orientation/non-Newtonian viscosity measuring process of the present invention.

The relationship between fluorescence anisotropy and molecular orientation has been examined in model development by several authors. (Nobbs et al., *Polymer*, 15, 287 (1974); Chappoy et al., *Methods of Experimental Physics*, Vol. 16A, Academic Press, New York (1980); and Jarry et al., *J. Poly. Sci., Poly Phys.*, 16, 443 (1978)). For purposes of the present invention a fluorescent chromophore is considered as depicted in FIG. 1, possessing a molecular axis, M, which is oriented at angles $\theta$ and $\phi$ with respect to the laboratory frame of reference. Here, $\theta$ is the azimuthal angle and, for the present experiments, z is the direction of flow.

The objective of the model calculations is to establish a relationship between average orientation moments, $\overline{\cos^2\theta}$ and $\overline{\cos^4\theta}$, and the measured fluorescence anisotropy. The usual definition of the anisotropy, r, is given as $$r = \frac{I_{vv} - I_{vh}}{I_t} \quad (1)$$

where $I_{vv}$ is a measured fluorescence intensity with vertically oriented excitation polarizer and emission analyzer, $I_{vh}$ is the intensity with vertical polarizer and horizontal analyzer, and $I_t$ is the total light intensity. In the discussion below, we will use other combinations of vertically and horizontally oriented polarized light to define an alternative anisotropy, r'.

Figure 2:
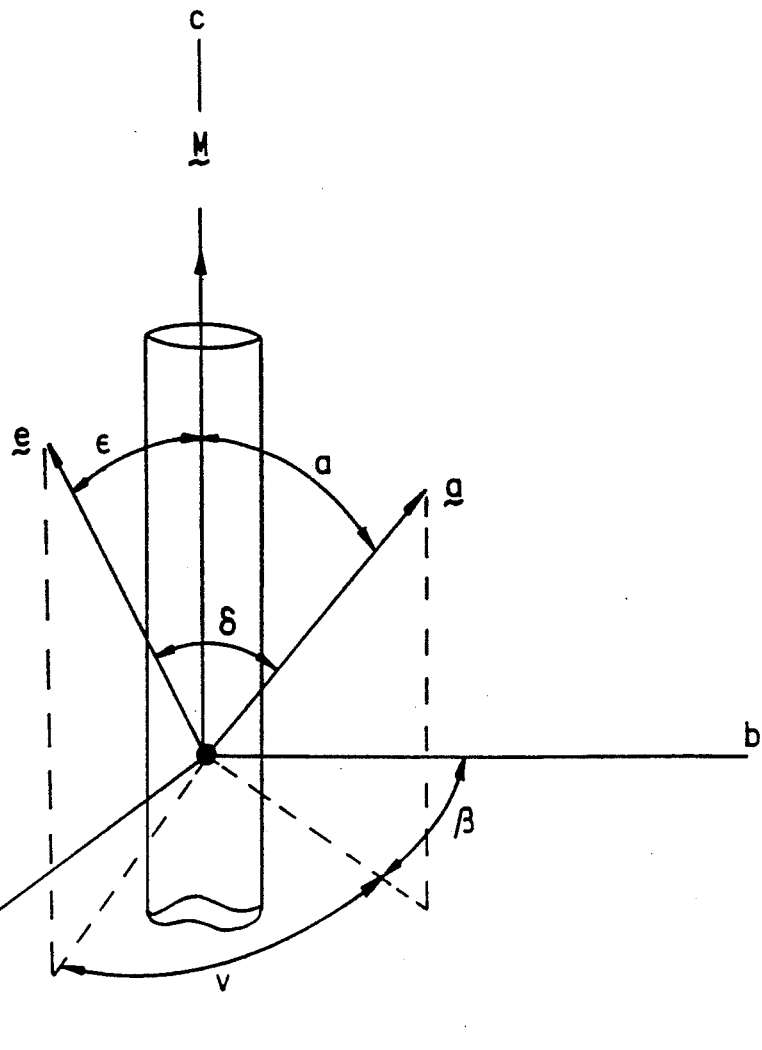
FIG. 2 is a molecular coordinate system illustrating the absorption and emission dipoles and their relationship to the molecular axis according to the present invention.

A molecular coordinate system shown in FIG. 2 was established where the molecular axis M is directed along the c axis and a and e are the absorption and emission dipoles at angles $\alpha$ and $\epsilon$ with respect to M. In general, $\alpha$ and $\epsilon$ are non-zero and unequal, but for anthracene, the chromophore of interest here, $\alpha = 0$ and $\epsilon \approx 0$. The relationship between observations in the laboratory frame of reference and the molecular frame of reference is obtained by making coordinate transformations which project a and/or $\theta$ onto the laboratory frame of reference. The fluorescence light intensities are determined in accordance with the directions of the polarizer and analyzer vectors P and A.

Following the development of Chappoy and DuPre, (*Methods of Experimental Physics*, Vol. 16A, Academic Press, New York (1980)), it was assumed that the orientation distribution function of the chromophores, $f(\theta)$, could be expressed as a sum of Legendre polynomials which, in general, depend on $\theta$ and $\phi$, but for the case of uniaxial flow along the z direction, it was assumed axial symmetry so that the distribution is independent of $\phi$. Since $f(\theta) = f(-\theta)$, only the even polynomial terms are present. The normalized distribution function is expressed as $$\int_{-1}^{1} f(\theta) d(\cos\theta) = 1. \quad (2)$$

The normalized fluorescence intensity is given by $$I_{ij} = \frac{1}{2\pi} \int_0^{2\pi} \int_0^{\pi} M_{ai}^2 M_{ej}^2 f(\theta) \sin\theta \, d\theta \, d\phi \quad (3)$$

where $I_{ij}$ is the emitted fluorescence intensity which results from an excitation light source polarized along the laboratory i axis and which passes through a polarization analyzer oriented in the direction of the laboratory j axis. $M_{ai}^2$ and $M_{ej}^2$ are the squares of the absorption and emission vectors which have been projected onto the laboratory axes i and j respectively via a coordinate transformation matrix, and $f(\theta)$ is the angular distribution function. This yields:

$$M_{ai}^2 = (a \cdot O \cdot P_i)^2 \quad (4)$$

and $$M_{ej}^2 = (e \cdot O \cdot A_j)^2 \quad (5)$$

where O is the transformation matrix, $$O = \begin{bmatrix} \cos\theta\cos\phi & \cos\theta\sin\phi & -\sin\theta \\ -\sin\phi & \cos\phi & 0 \\ \sin\theta\cos\phi & \sin\theta\sin\phi & \cos\theta \end{bmatrix} \quad (6)$$

Equations 3 through 6 express the physical sequence of events for light absorption and fluorescence emission. The absorption vector is brought into coincidence with a component of the polarized excitation light via the transformation operation of equation (4) and the reverse occurs during emission via equation (5).

The integrations of equation (3) yield a $3 \times 3$ matrix whose components are light intensities for various combinations of $P_i$ and $A_j$. Having evaluated the matrix, one can then calculate anisotropies in accordance with equation (1) where $I_{vv}$ becomes $I_{11}$, $I_{22}$ or $I_{33}$ and $I_{vh}$ becomes one of the off-diagonal terms. For example, when $\alpha = 0$ and $\epsilon = 0$, i.e., absorption and emission dipoles lie along the direction M, then vertically oriented light will be absorbed in proportion to $\cos^2\theta$. Equation (3) becomes an integral over all space of $\cos^4\theta$ weighted by the orientation function $f(\theta)$ resulting in $I_{33} = \overline{\cos^4\theta}$.

For anthracene, $\alpha = 0$, $\epsilon \neq 0$, and $\delta \neq 0$, where $\epsilon$ has been defined in FIG. 2, Chappoy and DuPre have evaluated the following matrix.

$$I = \begin{cases} \frac{3}{8}\cos^2\delta \sin^4\theta + \frac{1}{16}\sin^2\delta(3\sin^2\theta\cos^2\theta + \sin^2\theta) \\ \frac{1}{8}\cos^2\delta \sin^4\theta + \frac{1}{16}\sin^2\delta(\sin^2\theta\cos^2\theta + 3\sin^2\theta) \\ \frac{1}{2}\cos^2\delta \sin^2\theta\cos^2\theta + \frac{1}{4}\sin^2\delta(\cos^2\theta + \cos^4\theta) \end{cases} \quad (7)$$

$$\frac{1}{8}\cos^2\delta \sin^4\theta + \frac{1}{16}\sin^2\delta(\sin^2\theta\cos^2\theta + 3\sin^2\theta)$$

$$\frac{3}{8}\cos^2\delta \sin^4\theta + \frac{1}{16}\sin^2\delta(3\sin^2\theta\cos^2\theta + \sin^2\theta)$$

$$\frac{1}{2}\cos^2\delta \sin^2\theta\cos^2\theta + \frac{1}{4}\sin^2\delta(\cos^2\theta + \cos^4\theta)$$

-continued $$\left. \begin{array}{c} \frac{1}{2}\cos^2\delta \sin^2\theta \cos^2\theta + \frac{1}{4}\sin^2\delta \sin^4\theta \\ \frac{1}{2}\cos^2\delta \sin^2\theta \cos^2\theta + \frac{1}{4}\sin^2\delta \sin^4\theta \\ \cos^2\delta \cos^4\theta + \frac{1}{2}\sin^2\delta \sin^2\theta \cos^2\theta \end{array} \right\}$$

It is noted that the matrix contains orientation moments $\cos^2\theta$ and $\cos^4\theta$ as well as the term $\cos^2\epsilon$ which is a molecular property and does not depend on the orientation. The value of $\cos^2\epsilon$ is obtained from a separate experiment; its value for anthracene is 0.733 (Jarry et al., *Macromolecules*, 12, 927 (1979)). In general, two independent measurements of anisotropy must be made in order to calculate $\overline{\cos^2\theta}$ and $\overline{\cos^4\theta}$.

Figure 3A:
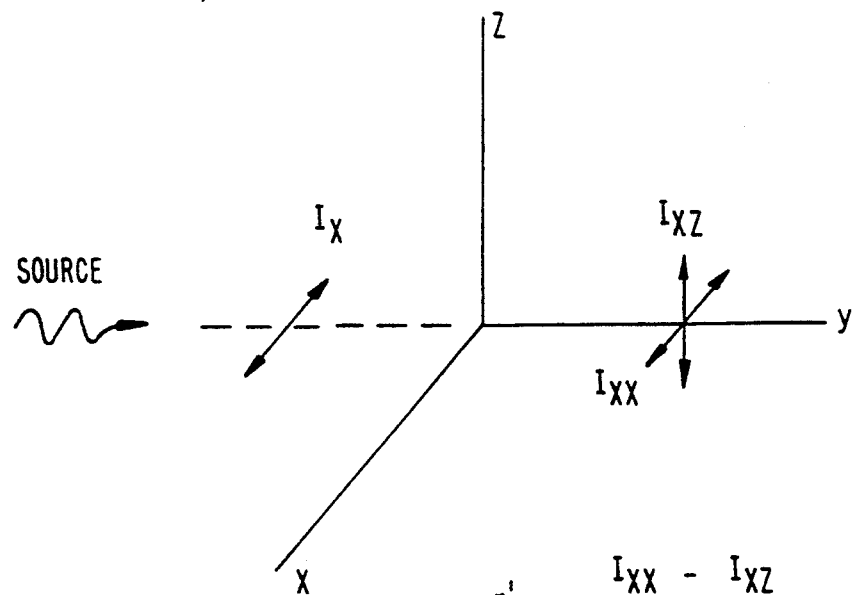
FIGS. 3A and 3B are schematic representation of the definition of the anisotropies r and r'.
Figure 3B:
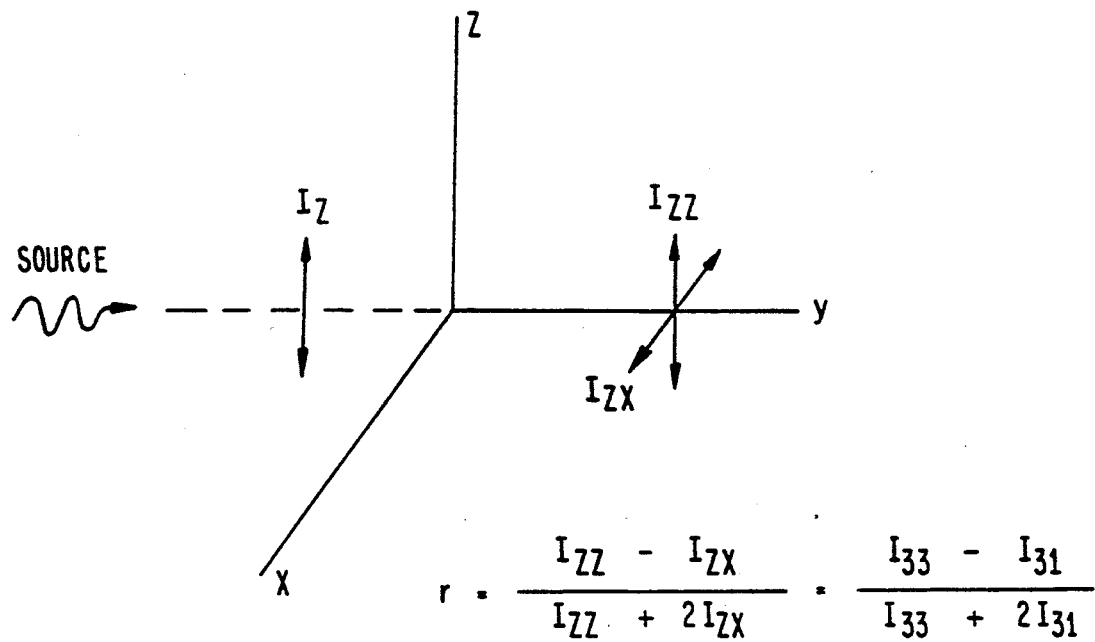

In the present invention a single optical fiber was used to excite and receive the fluorescence. The design consists of an optical fiber, discussed in detail below, which was inserted into the wall of a processing machine flush with the inside surface and used to probe the fluorescence in the near neighborhood. FIGS. 3A and 3B are schematic representations of the physics of the situation, i.e., excitation light polarized in the z or x direction propagates in the positive y direction and emission is observed along the y direction with the analyzer oriented in the z or x directions. Anisotropies r and r' are $$r = \frac{I_{zz} - I_{zx}}{I_{zz} - 2I_{zx}} = \frac{I_{33} - I_{31}}{I_{33} - 2I_{31}}, \quad (8)$$

$$r' = \frac{I_{xx} - I_{xz}}{I_{xx} - I_{xz}} = \frac{I_{11} - I_{13}}{I_{11} - I_{13}}, \quad (9)$$

where the denominator in equation (8) is the total light intensity. By substituting the elements of the matrix of equation (7) into equations (8) and (9), we obtain $$r = \frac{3\overline{\cos^4\theta} - \overline{\cos^2\theta}}{2\overline{\cos^2\theta}} \cdot \frac{3\cos^2\delta - 1}{2} \quad (10)$$

and $$r' = \frac{6 - 20\overline{\cos^2\theta} + 14\overline{\cos^4\theta}}{(5 - 6\overline{\cos^2\theta} + \overline{\cos^4\theta}) + (1 + 2\overline{\cos^2\theta} - 3\overline{\cos^4\theta})\cos^2\delta} \cdot \frac{3\cos^2\delta - 1}{2} \quad (11)$$

In deriving the above equations it has been assumed that the chromophore rotational relaxation time, $\tau_r$, is much longer than the fluorescence decay time, $\tau_d$. It is noted, however, that long rotational relaxation times were incorporated into the relaxation behavior of the chromophore by covalently bonding it to the main chain of polybutadiene. Such an effect has been observed by Jarry and co-workers (Jarry et al., *Macromolecules*, 12, 927 (1979) who found that, when anthracene was bonded to isoprene, its $\tau_r$ increased by two orders of magnitude and that $\tau_r > \tau_d$. In general, when the rotational relaxation is taken into account, the expression for anisotropy is $$r = F(\overline{\cos^2\theta}, \overline{\cos^4\theta}) \cdot G(\cos^2\delta) \cdot (\tau_d/\tau_r + 1)^{-1}, \quad (12)$$

where F expresses the effect of orientation, G expresses the dependence on the angle $\delta$, and the last term expresses the effect of the rotational relaxation. If $\tau_r \gg \tau_d$, then $(\tau_d/\tau_r + 1)^{-1} \approx 1$.

Figure 4:
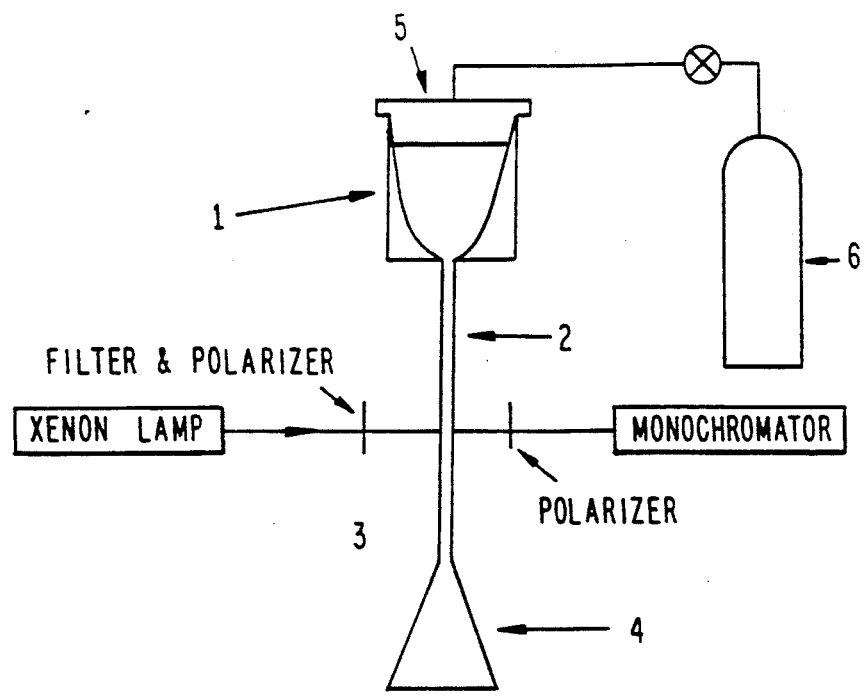
FIG. 4 is a schematic diagram of the capillary flow apparatus according to one embodiment of the present invention.

The experimental design of the apparatus used to measure fluorescence anisotropy consisted of using a capillary flow apparatus and a Weissenberg rheometer to make simultaneous measurements of non-Newtonian viscosity and fluorescence anisotropy as a function of shear rate. The capillary flow apparatus, which is diagrammed schematically in FIG. 4, was incorporated into a commercial fluorimeter. The capillary flow apparatus consists of a glass reservoir vessel 1 with a capacity of 500 cm$^3$ which sits at the head of a vertically oriented capillary 2. The capillary extends through the sample chamber 3 of the fluorimeter and is connected to a collection vessel 4 at the bottom end. Capillary diameters of 1 or 2 mm are used with a length of approximately 25 cm. Both are made of borosilicate glass which transmits excitation light with wavelengths as short as 350 nm. The reservoir at the head of the capillary is surrounded by a brass pressure vessel 5 which can be pressurized with a source of nitrogen gas 6 up to $7 \times 10^5$ Pa (100 psi). The pressure was measured using a resistance type pressure transducer.

The shear rate experienced by the liquid in the capillary was varied by changing the pressure. The classical equations of capillary flow for a Newtonian fluid were used:

$$\eta = \frac{\pi R^4}{8Q} \cdot \frac{\Delta P}{L} \quad (13)$$

and $$\dot{\gamma} = \frac{4Q}{\pi R^3} \quad (14)$$

where $\eta$ is the viscosity, R is the radius of the capillary, P is the pressure difference across the ends of the capillary, Q is the flow rate, L is the length of the capillary, and $\dot{\gamma}$ the shear rate. Q, the flow rate of material through the capillary, is obtained by measuring the amount of material eluted from the capillary in a given time period.

Figure 5:
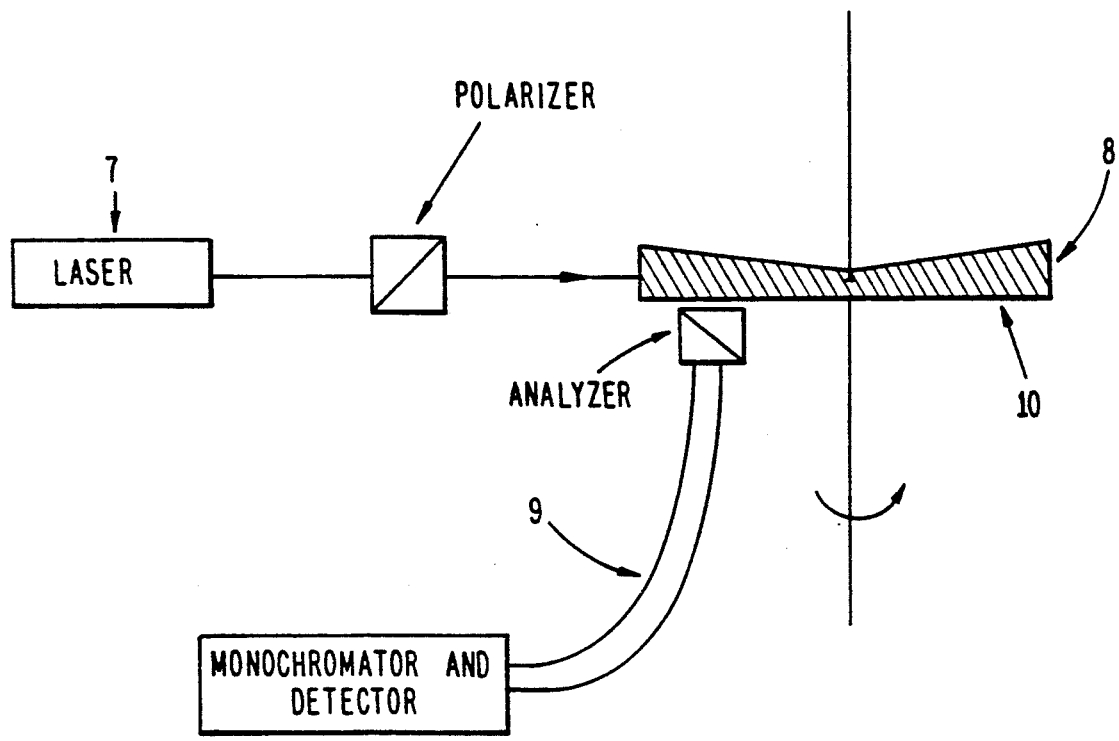
FIG. 5 is a schematic diagram of the optically instrumented Weissenberg rheometer according to the present invention.

A Weissenberg cone and plate rheometer was also being used in the present invention This equipment has been instrumented so that fluorescence anisotropy measurements can be made simultaneously with the rheological measurements. The apparatus is depicted in FIG. 5. Excitation light energy from an argon ion laser 7 was directed to the specimen 8 between the cone and plate. The fluorescence spectra is collected at 180° by an optical fiber 9 which sits below the optically transparent polymethylmethacrylate plate 10. In the process, the cone rotates but the plate remains stationary.

In initial experiments, the capillary apparatus was used to measure viscosity and fluorescence anisotropy of a low molecular weight polybutadiene doped with the labelled polybutadiene at a concentration of 10$^{31}$ $^5$ molar. The number average molecular weight of the polybutadiene was 2800 while the number average molecular weight of the labelled polybutadiene was 12,000. The low molecular weight of the specimen, 2800, is below the entanglement molecular weight, 6000, for polybutadiene so that the rheological polymeric effects would not be observed. This experiment was carried out in order to obtain a frame of reference for the behavior of a Newtonian material before proceeding with the non-Newtonian material.

The non-Newtonian polymer studied is also polybutadiene but with a weight average molecular weight of 420,000, i.e., well above the entanglement value. This specimen was also doped with the labelled polybutadiene at a concentration of $10^{-5}$ molar.

The following examples are presented to illustrate the invention which is not intended to be considered as being limited thereto. In the examples and throughout percentages are by weight unless otherwise indicated.

EXAMPLE 1

A fluorescence spectrum for the anthracene labelled polybutadiene as a dopant in the low molecular weight ($M_n=2800$) polybutadiene was obtained for an excitation wave length of 398 nm using a commercial fluorimeter. The anisotropy measurements, calculated according to equation (1), were made over a wavelength range from 420 to 470 nm and for a pressure range from 0 to 50 psi. The viscosity and shear rate were obtained using equations (13) and (14).

Viscosity and fluorescence anisotropy as a function of shear rate for the doped low molecular weight ($M_n=2800$) polybutadiene was also obtained. It is noted that this material is Newtonian in its behavior over the range of shear rates from 20 to 70 $s^{-1}$. The anisotropy, which is also constant, correlated with the Newtonian behavior. The interpretation of the data obtained indicated that, within the limits of uncertainty of measurements, molecular orientation is not seen in the fluorescence anisotropy for Newtonian polymer melts. Since the molecular weight of this specimen is below the entanglement value, the molecule is pictured as tumbling in the velocity field of the capillary, but, on the average, the molecule remains unextended.

In order to measure viscosities of process polymer melts and/or solutions undergoing shear flow an optical probe was designed to have a "standardized" size so as to enable the probe to be inserted into existing temperature and/or pressure probe ports on polymer processing equipment.

Figure 6:
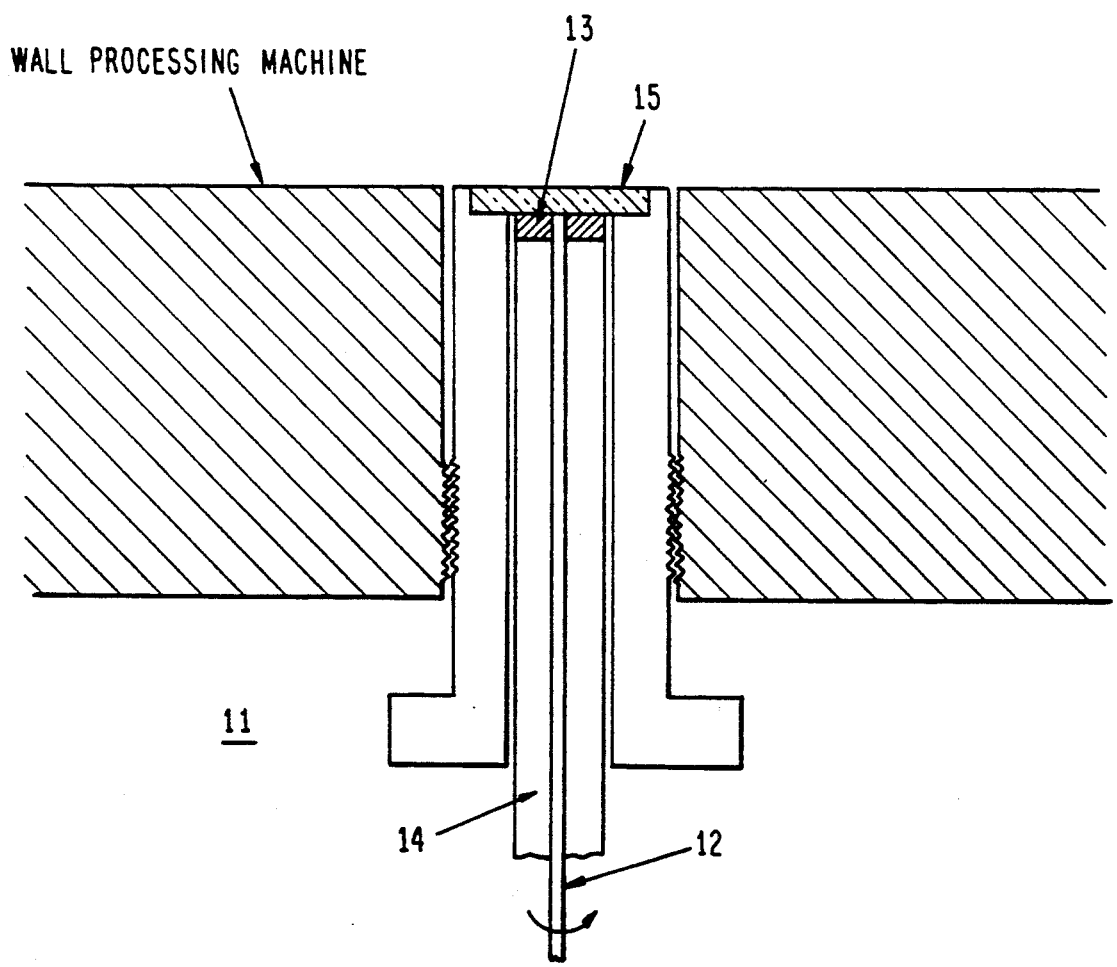
FIG. 6 is an illustration of the optical probe utilized in conjunction with polymer processing machinery according to one embodiment of the present invention.

As illustrated in FIG. 6, the probe consists of a bifurcated optical fiber 11 which contains a bundle of 19 fibers. At the common end, the central fiber 12 is inserted through a hole in a polarizer 13 and carries polarized excitation light to the specimen. The other 18 fibers 14 terminate at the polarizer and are used to carry the fluorescence light to the detector. Mechanical orientation of the central fiber, by any known means for transmitting rotational movement rotates the polarization axis of the incident light. Mechanical orientation of the polarizer with respect to the fiber bundle rotates the axis of the fluorescence radiation analyzer. By appropriately setting the relative orientations of the central excitation fiber and the fluorescence analyzer, measurements of anisotropies r and r' are made.

Although illustrated in a particular embodiment including a total of 19 optical fibers including a central excitation optical fiber, the probe may include any number of excitation and collector fibers. Moreover, the excitation fiber need not be centrally located with respect to the collection fibers. In this regard, the excitation and collector fibers need only terminate at the respective polarizer 13 and window 15 of the probe assembly. The illustrative embodiment of FIG. 6 is merely a preferred embodiment designed to allow the probe to be inserted into existing temperature and/or pressure probe ports by suitable connecting means.

Plotted values of anisotropy and shear viscosity vs. shear rate for low molecular weight PBOH doped with the tagged polybutadiene indicate that because the molecular weight of PBOH is below the entanglement molecular weight, the behavior of this material is Newtonian. This characteristic is reflected in the anisotropy which is independent of shear rate. Although the tagged polymer has a molecular weight greater than entanglement value, the matrix polymer has no entanglements. Thus, the tagged polymer is found to be dispersed throughout the matrix PBOH with random orientation.

The tagged polybutadiene can be used in any matrix polymer system with which it is compatible and into which it can be doped without phase separation. Two polymers which were used to demonstrate this concept and the measurement principle were high molecular weight butadiene plasticized with 5% cetane (PB/Cetane) and a low molecular weight polybutadiene (PBOH). Plotted values of viscosity vs. shear rate dependence of these polymers indicated that the PB/Cetane is non-Newtonian and the PBOH is Newtonian over a range of shear rates of $10^{-2.6}$ to 100 $sec^{-1}$. The molecular weight of the polybutadiene in the PB/Cetane sample is much greater than its entanglement molecular weight whereas for PBOH, the molecular weight is less than the entanglement value.

In plotting on a log-log scale, values of shear stress, shear viscosity, and fluorescence anisotropy vs. shear rate for PB/Cetane which has been doped with the tagged polybutadiene, it was noted that the anisotropy decrease and shear stress increase with increasing shear rate, and that viscosity decreases with shear rate. Utilizing a calibration chart one can easily obtain a value for the shear viscosity by measuring the anisotropy.

By plotting the same anisotropy data above on a linear-log scale, along with anisotropy measurements for PB/Cetane which has been doped with free anthracene it was found that anisotropy is independent of shear rate for the free anthracene. This indicates that, without the ability to associate with the matrix polymer, the free anthracene assumes a random orientation in the molecular environment.

Although the invention has been described with reference to particular means, materials and embodiments, from the foregoing description, one skilled in the art can ascertain the essential characteristics of the present invention and various changes and modifications may be made to adapt the various uses and characteristics thereof without departing from the spirit and scope of the present invention as described in the claims that follows.

We claim:

1. A method for measuring fluid properties of a polymer melt undergoing shear or extensional flow which comprises:

incorporating a chromophore into the matrix of a polymer so that said chromophore is responsive to changes in the molecular orientation of said polymer, said chromophore comprises a polymeric chromophore having a polymer backbone and a chromophore bonded to said polymer backbone;

exposing said polymer to fluorescent excitation while subjecting said polymer to shear or extension stress;

detecting fluorescent emission spectra which results from said fluorescent excitation and;

analyzing said fluorescent emission spectra to determine fluid properties of said polymer.

2. A method for measuring fluid properties of a polymer melt according to claim 1, wherein said fluid properties are selected from the group consisting of non-Newtonian viscosity, molecular orientation, shear rate, extensional rate, shear stress, extensional stress and combinations thereof.

3. A method for measuring fluid properties of a polymer melt according to claim 2 wherein said fluid property consists of non-Newtonian viscosity.

4. A method for measuring fluid properties of a polymer melt according to claim 1, wherein said fluorescent spectra emission comprises fluorescence anisotropy.

5. A method for measuring fluid properties of a polymer melt according to claim 4, wherein said amount of chromophore is between about $10^{-4}$ and about $10^{-6}$ molar concentration.

6. A method for measuring fluid properties of a polymer melt according to claim 1, wherein said chromophore is added in an amount less than that which would effect said fluid property of said polymer being measured.

7. A method for measuring fluid properties of a polymer melt according to claim 1, wherein said chromophore comprises a bifunctional anthracene which is bonded to polybutadiene.

* * * * *